US007416698B2

(12) United States Patent
Smith et al.

(10) Patent No.: US 7,416,698 B2
(45) Date of Patent: Aug. 26, 2008

(54) MOLECULAR TOPOLOGICAL FRACTIONATION OF MACROMOLECULES

(75) Inventors: Patrick B. Smith, Midland, MI (US);
David M. Meunier, Midland, MI (US);
Scott A. Baker, Lake Jackson, TX (US);
Robert K. Prud'homme, Lawrenceville, NJ (US)

(73) Assignee: Dow Global Technologies Inc., Midland, MI (US)

( * ) Notice: Subject to any disclaimer, the term of this patent is extended or adjusted under 35 U.S.C. 154(b) by 806 days.

(21) Appl. No.: 10/510,060

(22) PCT Filed: May 14, 2003

(86) PCT No.: PCT/US03/15148

§ 371 (c)(1),
(2), (4) Date: Oct. 4, 2004

(87) PCT Pub. No.: WO03/098208

PCT Pub. Date: Nov. 27, 2003

(65) Prior Publication Data

US 2005/0176154 A1    Aug. 11, 2005

(51) Int. Cl.
*G01N 30/02* (2006.01)
(52) U.S. Cl. .............................. 422/70; 702/23; 702/30; 210/656
(58) Field of Classification Search .................. 422/70; 702/23, 30; 210/656
See application file for complete search history.

(56) References Cited

U.S. PATENT DOCUMENTS 4,112,032 A     9/1978   Blaszyk et al.
4,775,943 A  *  10/1988  Chamberlin et al. .......... 702/30
6,294,388 B1    9/2001   Petro

FOREIGN PATENT DOCUMENTS

WO     WO 99/42489    *  8/1999

OTHER PUBLICATIONS

H. Yun, S.V. Olesik and E.H. Marti, J. Microcolumn Separations 11:53-61, 1999.*

(Continued)

*Primary Examiner*—Mikhail Kornakov
*Assistant Examiner*—Timothy G Kingan
(74) *Attorney, Agent, or Firm*—The Dow Chemical Company; Burke M. Halldorson; Claude F. Purchase

(57) ABSTRACT

A process for characterizing a sample comprising a population of linear macromolecules of interest (104) and a population of long chain branched macromolecules of interest (103), the process including four steps. The first step is to provide a flow through separating medium (100) and a liquid eluant (101) in which the macromolecules of interest dissolve, the separating medium defining flow through channels (102), the eluant flow rate and the average diameter of the channels being in a range so that the linear macromolecules of interest elute before the long chain branched macromolecules of interest (105) (106). The second step is to introduce a sample into the liquid eluant. The third step is to flow the liquid eluant under pressure through the channels (102) of the separating medium (100). The fourth step is to differentiate the linear macromolecules of interest (104) from the long chain branched macromolecules of interest (103) based on their successive elution volumes established in the third step such as by determining the refractive index of the successive elution volumes or by subjecting the successive elution volumes to size exclusion chromatography.

10 Claims, 5 Drawing Sheets

OTHER PUBLICATIONS

K. Cabrera et al., J. High Resol. Chromatogr., 2000, 23, (1) 93-99.
Q. Ching Wang et al., Anal. Chem., 1993, 65, 2243-2248.
Frantisek Svec et al., Ind. Eng. Chem. Res., 1999, 38, 34-48.
Markus Gerle et al., Macromoleules, 1999, 32, 2629-2637.
W. W. Graessley et al., Macromolecules, 1976, 9 (1), 127-141.
M. De Pooter et al., J. of Applied Polymer Science, 1991, 42, 399-408.
M. Muthukumar et al., Macromolecules, 1989, 22, 1937-1941.
Norio Ishizuka et al., J. of Chromatography A, 1998, 797, 133-137.
Fred E. Regnier, J. High Resol. Chromatogr. 2000, 23, (1) 19-26.
Miroslav Petro et al., J. of Chromatography A, 1996, 752, 59-66.
Miroslav Janco et al., J. of Polymer Science: Part A: Polymer Chem., 38, 2000, 2767-78.
Donna J. Frater et al., J. of Polymer Science: Part B: polymer Physics, 35, 1997, 141-151.
S. Podzimek et al., J. of Applied Polmer Science, 81, 1588-1594 (2001).
Jiro Kumaki et al., J. Am. Chem. Soc., 1996, 118, 3321-3322.
Svetlana Prokhorova et al., Macromolecules, 1999, 32, 2653-2660.
Timothy von Werne et al., J. Am. Chem. Soc., 1999, 121, 7409-7410.
Isabelle Gusev et al., J. of Chroma. A. 855 (1999, 273-290.
E.E. Drott et al., J. of Poly. Sci.: Part a-2, 8, 1373-1385, 1970.
Gerrit Stegeman et al., J. of Chrom. A, 657, 1993, 283-303.
Hamish Small, J. of Colloid and Interface Science, vol. 48, No. 1, 1974.
T.A.J. Duke et al., Physical Review Letters, vol. 80, No. 7, 1552-1555, 1998.
David L. Smisek et al., Science, vol. 248, 1221-1223, 1990.
J. Brandrup and E.H. Immergut, Polymer Handbook, 1989, John Wiley & Sons.
J. Janca, Field-Flow Fractionation —Analysis of Macromolecules and Particles, 1988, Marcel Dekker.
J. C. Randall, NMR and Macromolecules, ACS, Washington, D.C., 1984, Chapter 9.
C. W. Macosko, Rheology, Principles, Measurements, and Applications, Wiley-VCH, New York, 1994, p. 505.
J. Calvin Giddings, Unified Separation Science, Wiley & Sons, Inc., New York, 1991.
R. K. Iier, The Chemistry of Silica, Wiley & Sons, Inc, New York, 1979, pp. 539-544.
W.W. Yau et al., Modern Size-Exclusion Liquid Chromatography, 1979, Wiley & Sons, Inc.
Hahnfeld, et al., *Applications of Anionic Polymerization Research*, Quick, Ed., ACS Symposium Series 696, pp. 167-184, 1996.
E. Heftmann Ed., *Chromatography Fundamentals and applications of chromatographic and electrophoretic methods*, vol. 22A, 1983, pp. A38-39.

* cited by examiner

MOLECULAR TOPOLOGICAL FRACTIONATION OF MACROMOLECULES

TECHNICAL FIELD

The instant invention is in the field of chemical analysis. More specifically, the instant invention relates to chemical analysis methods for the characterization of branching topology of macromolecules.

BACKGROUND ART

Common polymers, such as polystyrene or polyethylene, theoretically comprise extended linear chains of monomers. However, such polymers can also have branches; see Graessley et al., Macromolecules, Vol. 9, No. 1, 1976, p 127. Such branched polymers often have significantly better processing characteristics (especially when the number of monomer units in the branch chain exceeds 100 to 300 units) than their linear or short chain branched counterparts. For example, the melt strength of a long chain branched polymer can be significantly higher than the melt strength of its linear or short chain branched counterpart of the same molecular weight and often shear thin to a greater extent, see Macosko, Rheology—Principles, Measurements, and Applications, pages 497-506. Polymers that exhibit higher melt strength have superior processing properties and can command a higher price.

Polymer characterization is an important branch of chemical analysis. Characterization of a polymer to determine its topology, (in other words, the degree and type of branching of the polymer) is currently insufficient for correlating molecular structure to physical properties. Nuclear Magnetic Resonance (NMR) analysis can determine the average number of branch points per polymer molecule; see DePooter, et al., J. App. Pol. Sc., 42, p 399-408 (1991). However, such an NMR analysis does not determine the molecular weight distribution of the long chain branches or the type of branching, for example, "T" branching, "star" branching, "comb" branching and "T" branching.

Polymers have been characterized by Field Flow Fractionation (FFF) by flowing a solution of a polymer in a channel perpendicular to a force field (such as a centrifugal force field in a centrifuge) to separate the components of the polymer in successive elution volumes from the channel. See, for example, Janca, Field-Flow Fractionation—Analysis of Macromolecules and Particles, 1988, Marcel Dekker. In FFF, higher molecular weight fractions of the polymer generally elute from the channel after the lower molecular weight fractions of the polymer. FFF has not apparently been used to characterize polymers for long chain branching topology.

Ionic polymers, such as sulfonated polystyrene, have been characterized by electrophoresis (EP) in a system where the polymer is dissolved in a buffer solution and migrated under the influence of an electric field (electrophoretic mobility) through a medium such as a gel swelled with the buffer. Lower molecular weight fractions of the polymer migrate faster than higher molecular weight fractions of the polymer. The characterization of long chain branching of ionic polymers has been attempted using EP but without success. See Smisek and Hoagland, Science, 8 Jun. 1990, p 1221-1223 and especially page 1222, third column, which stated: "We next compared the dependence of [electrophoretic] mobility on N [molecular weight] for linear and star PSS [linear and star branched sulfonated polystyrene] (FIG. 4). Surprisingly, over the molecular size range displayed [N from about 100 to about 100,000], the mobility depended only on N, and was independent of molecular topology", in other words, no separation of linear from branched polymer was observed.

Hydrodynamic Chromatography (HDC) is an important polymer characterization technique. See, for example, Small, J. Colloid Interface Science, 1974, 48, p 147 and Stegeman et al., J. Chrom., 1993, 657(2), p 283-303. In HDC a solution of a polymer is flowed by an eluant over the surfaces of non-porous beads packed in column (or through a capillary column). In HDC the higher molecular weight fractions of the polymer elute from the column before the lower molecular weight fractions of the polymer. More accurately, HDC separates components of a polymer according to their hydrodynamic size in a solution or a dispersion. However, HDC has not apparently been used to characterize polymers for long chain branching topology.

Size Exclusion Chromatography (SEC) (also called Gel Permeation Chromatography (GPC)) is an important polymer characterization technique. See, Yau et al., Modern Size-Exclusion Liquid Chromatography, 1979, John Wiley & Sons. In SEC a solution of a polymer is flowed by an eluant through a column packed with porous beads. The polymer diffuses into and out of the porous beads (there being essentially no flow of the eluant through the porous beads because the flow channels around the beads are significantly larger than the pores of the beads). In SEC the higher molecular weight fractions of the polymer elute from the column before the lower molecular weight fractions of the polymer. More accurately, SEC separates components of a polymer according to their hydrodynamic size.

A branched polymer has a somewhat smaller radius of gyration in solution than a linear polymer of the same type and molecular weight. Thus, SEC can be used to characterize a polymer for branching. See Drott and Mendelson, Journal of Polymer Science, Part A-2, Vol. 8, 1970, p 1361. However, as pointed out by Drott and Mendelson, as the degree of branching of a polymer increases the relative effect on SEC elution volume decreases. Furthermore, SEC provides no direct information of the shape of the molecule (for example, star shape or H shape) or the molecular weight of the branch. Thus, the information obtained from SEC for the study of long chain branching of polymers is not sufficient to define the Theological properties of the polymer. It would be a clear advance in the art if a better solution were discovered for the problem of characterizing a polymer for long chain branching.

DISCLOSURE OF INVENTION

The instant invention is called "Molecular Topological Fractionation" (MTF). MTF provides a better solution for the problem of characterizing a polymer for long chain branching topology. MTF is a fundamentally new separation science technique as illustrated by reference to FIG. 1. FIG. 1 shows a plot of channel size divided by molecule size on the vertical axis versus channel flow rate on the horizontal axis. FIG. 1 shows the area occupied by various polymer characterization techniques, namely: Field Flow Fractionation (FFF), Hydrodynamic Chromatography (HDC), Gel Permeation Chromatography (GPC), Electrophoresis (EP) as well as the technique of the instant invention (MTF).

As shown in FIG. 1, the channel size divided by the molecule size (the molecule size being expressed as the radius of gyration of the polymer in solution) of GPC and EP can vary from a relatively small value to a relatively large value depending on the pore size and pore size range used in the GPC packing or the gel concentration used in EP. However, in both GPC and EP there is little or no flow of liquid through the pores of the GPC packing or through the gel of the EP system. With regard to FFF, the channel size is large relative to the molecule size and the channel flow rate is relatively fast. In HDC, the channel size is smaller than in FFF and the channel flow rate is generally (but not necessarily) relatively fast. In MTF, the channel size is relatively small in relation to the molecule size and the channel flow rate is relatively slow.

More specifically the instant invention is a process for characterizing a sample comprising a population of linear macromolecules of interest and a population of long chain branched macromolecules of interest, the process characterized by the following four steps. The first step is to provide a flow through separating medium and a liquid eluant in which the macromolecules of interest dissolve, the separating medium defining a multiplicity of flow through channels which are small enough in diameter so that when the eluant containing dissolved sample macromolecules of interest is caused to flow under pressure through the channels of the separating medium, over a certain linear velocity range, a select fraction within the population of the linear macromolecules of interest will elute before a select fraction of the population of the long chain branched macromolecules of interest whereby separate peak elution volumes of said fractions of linear macromolecules and long chain branched macromolecules of interest is established for producing differentiation of the fraction of linear macromolecules from the fraction of long chain branched macromolecules, said select fractions being of similar size, the similar size of the fractions of interest being characterized so that these fractions will co-elute in a size exclusion chromatography experiment optimized so that the fractions are separated by hydrodynamic size, and wherein the separation is conducted under temperature and solvent conditions which produce equivalent results to that obtained when the separation is conducted under isothermal and isocratic conditions. The second step is to introduce a sample of dissolved linear macromolecules of interest and long chain branched macromolecules of interest into the liquid eluant. The third step is to flow the liquid eluant under pressure through the channels of the separating medium at a linear velocity that is within the range specified in the first step, whereby the sample macromolecules of interest emerge from the separating medium separated into successive elution volumes of the liquid eluant, characterized by said linear macromolecules of interest eluting before said similarly sized long chain branched macromolecules of interest. The fourth step is to differentiate the linear macromolecules of interest from the long chain branched macromolecules of interest based on their successive elution volumes established in the third step.

MODES FOR CARRYING OUT THE INVENTION

Figure 11:
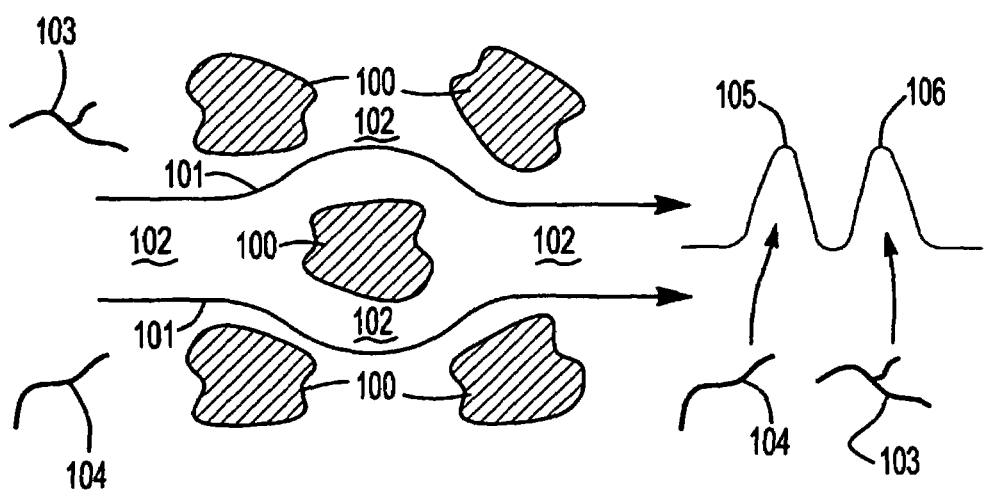
FIG. 11 is a schematic depiction summarizing the central features of the process of the instant invention.

Referring now to FIG. 11, the central features of the process of instant invention will be summarized. As discussed below in greater detail, the instant invention is a process for characterizing a sample comprising a population of linear macromolecules of interest and a population of long chain branched macromolecules of interest. The first step is to provide a flow through separating medium 100 and a liquid eluant 101 in which the macromolecules of interest dissolve. The separating medium defines a multiplicity of flow through channels 102. A long chain branched macromolecule 103 and a linear macromolecule 104 of the same size dissolved in the eluant 101 are flowed through the channels 102 and then elute from the separating medium 100 in different elution volumes of the eluant 101 (and if not completely separated, then at least they have different peak elution volumes). The linear macromolecule 104 elutes first and is detected as chromatographic peak 105. The long chain branched macromolecule elutes later and is detected as chromatographic peak 106.

Figure 1:
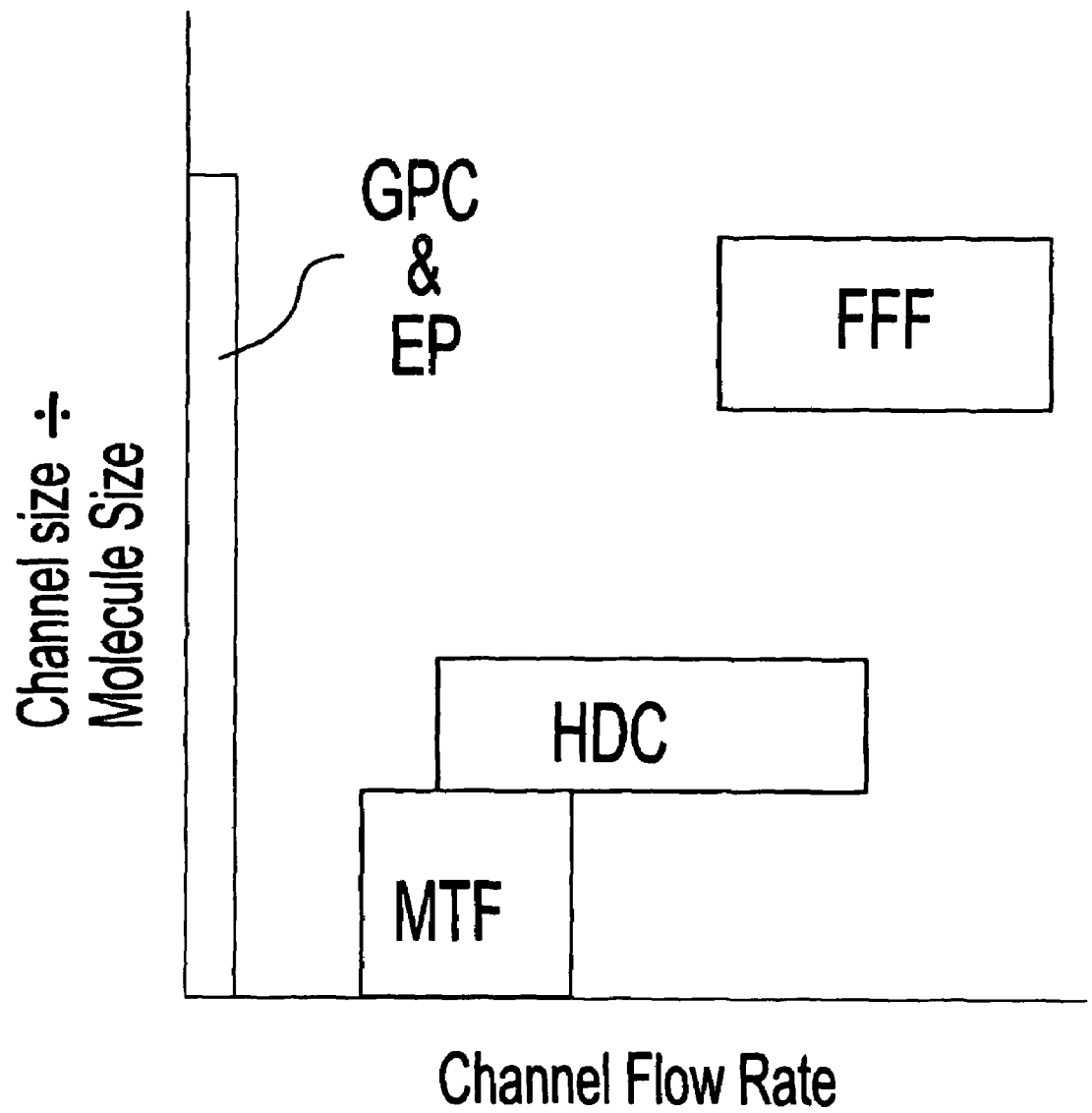
FIG. 1 is a plot of channel size divided by molecule size v. channel flow rate for the technique of the instant invention and for various prior art techniques.
Figure 2:
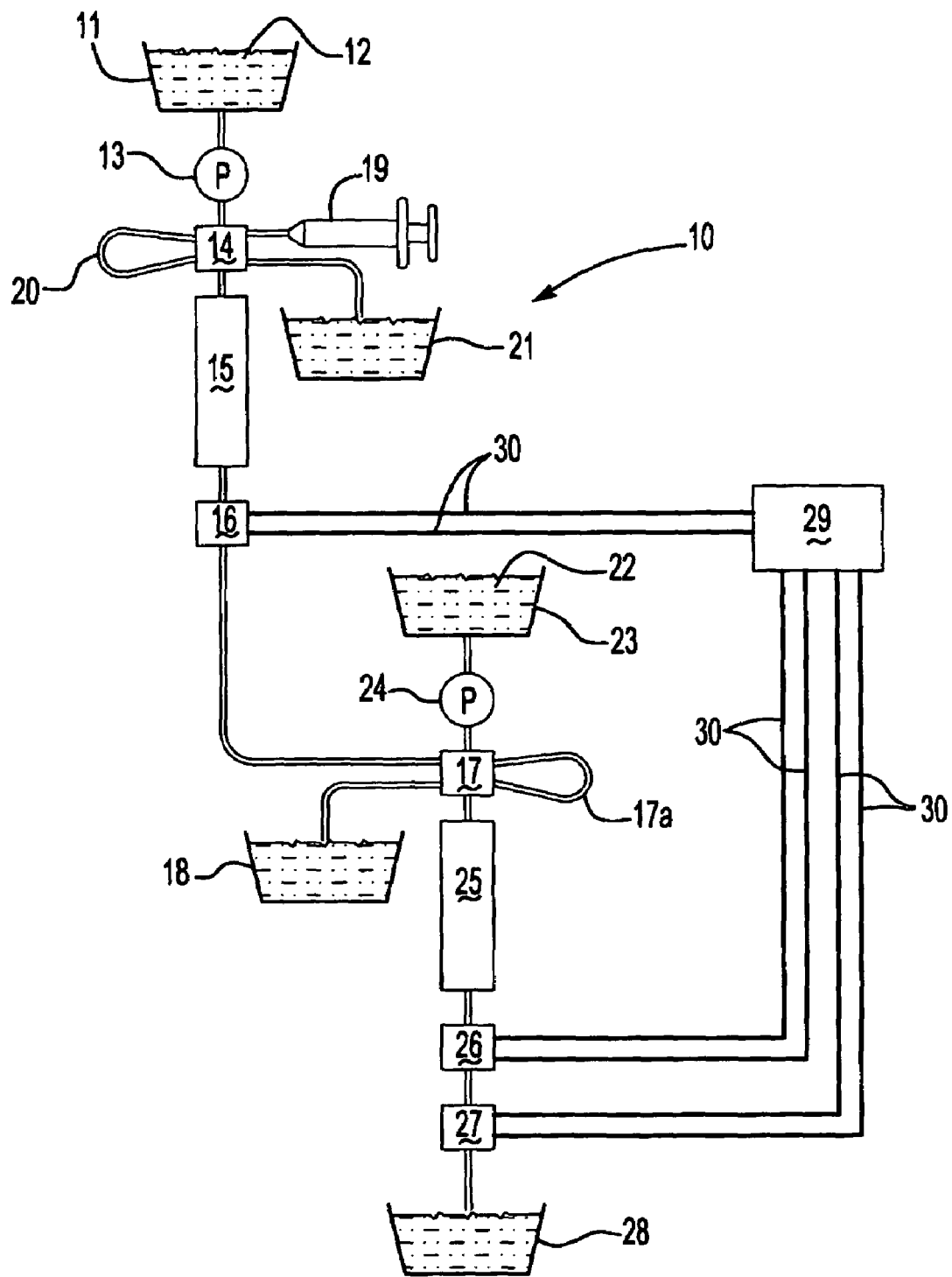
FIG. 2 is a schematic drawing of an apparatus that can be used to practice the process of the instant invention.

Referring now to FIG. 2, therein is shown apparatus 10 that can be used to practice the process of the instant invention. The apparatus 10 includes a first reservoir 11 for containing a liquid eluant 12. The liquid eluant 12 is flowed by first pump 13 through first injection valve 14, through a porous separating medium contained in first column 15, through first detector 16, through second injection valve 17, through second loop 17a and then to second waste reservoir 18. The detector 16 is responsive to the concentration of polymer in the liquid eluant 12, for example, a refractive index detector.

The polymers to be separated (which in general are a blend of linear and long chain branched polymers, in other words, the polymers to be separated comprise a population of linear macromolecules of interest and a population of long chain branched macromolecules of interest) are dissolved in a solvent to form a solution of the polymers in a solvent and placed in syringe 19 connected to the first injection valve 14 so that the solution of the polymers in a solvent can be flowed through a first injection loop 20 and then to a first waste reservoir 21. The specific solvent and liquid eluant used in the instant invention is not critical but preferably the solvent and liquid eluant are the same and are thermodynamically good solvents for the polymers to be separated, in other words, the Mark-Houwink-Sakurada equation alpha exponent value being greater than 0.5 (preferably greater than about 0.7), see Brandrup and Immergut, Polymer Handbook, 1989, John Wiley & Sons. By definition herein, a long chain branched polymer is a polymer having at least one branch consisting of at least twenty monomer units (more preferably at least 100 monomer units and most preferably more than 300 monomer units). The term "macromolecule" used herein means a synthetic polymer such as polystyrene or polyethylene; a natural polymer such as a polysaccharide, a polypeptide or a hydrocarbon such as a polyisoprene; or a semisynthetic polymer such as rayon. When the first injection valve 14 is rotated from its loop loading position to its loop injection position, the solution of the polymers in a solvent contained in the first loop 20 is flowed through the porous separating medium contained in the first column 15, through the first detector 16, through the second injection valve 17, through second loop 17a and then to the second waste reservoir 18 by the flow of liquid eluant.

Many different types of porous separating media can be used in the instant invention. For example, the porous separating medium can be a porous monolithic packing, see Gusev et al., J. Chrom. A, 855 (1999) 273-290. Porous monolithic packing columns are sold commercially by Isco, Inc. The porous medium can also simply be a bed of particles of essentially the same size or differing size. The porous medium can also be a monolithic packing composed of an open cell foam structure. The porous medium can also be a porous ceramic material (for example a porous silica or a zeolitic material) having appropriate pore or channel size.

Although the type of porous separating medium contained in the first column 15 is not critical in the instant invention, the following requirements are necessary. The separating medium must define a multiplicity of flow through channels which are small enough in diameter so that when the eluant containing dissolved sample macromolecules of interest is caused to flow under pressure through the channels of the separating medium, over a certain linear velocity range, a select fraction within the population of the linear macromolecules of interest will elute before a select fraction of the population of the long chain branched macromolecules of interest whereby separate peak elution volumes of said fractions of linear macromolecules and long chain branched macromolecules of interest is established for producing differentiation of the fraction of linear macromolecules from the fraction of long chain branched macromolecules, said select fractions being of similar size, the similar size of the fractions of interest being characterized so that these fractions will co-elute in a size exclusion chromatography experiment optimized so that the fractions are separated by hydrodynamic size, and wherein the size exclusion chromatography separation is conducted under temperature and solvent conditions which produce equivalent results to that obtained when the size exclusion chromatography separation is conducted under isothermal and isocratic conditions.

The term "isocratic" means that the solvent composition of the eluant used in the size exclusion chromatography separation is constant. The term "equivalent" means essentially the same result, in other words, that the fraction of linear macromolecules and the fraction of long chain branched macromolecules of similar size or radius of gyration co-elute in the size exclusion chromatography experiment. Preferably, the size exclusion chromatography experiment is conducted under isothermal and isocratic conditions.

The linear macromolecules of interest can be differentiated from the long chain branched macromolecules of interest by quantifying the concentration of same in each successive elution volume. For example, the refractive index detector 16 is responsive to the concentration of macromolecules of interest in the successive elution volumes from the column 15.

Although the diameter of an individual channel of the separating medium can be smaller than the radius of gyration of a long chain branched macromolecule of interest, at least a portion of the channels need to have a diameter large enough so that such macromolecule of interest can be flowed through the channels of the separating medium. On the other hand, if none of the channels of the separating medium are sufficiently small in diameter, then there will not be the required separation between the long chain branched macromolecule and the linear macromolecule. The channels of the separating medium of the instant invention can have and often will have a range of diameters. However, such range of diameters should not be so large that essentially all of the flow of eluant is through large diameter channels that are not sufficiently small to produce the separation between the long chain branched macromolecule and the linear macromolecule required by the instant invention.

Preferably, the log of the weight average molecular weight (WAMW) of a long chain branched polymer of interest in the sample to be characterized in grams per mole divided by the effective pore diameter (EPD) in angstroms (log [WAMW÷EPD]) of the porous separating medium cross-sectioned perpendicular to the direction of flow of the eluant through the porous separating medium is in the range of from about 1 to about 4 and more preferably in the range of from about 2 to about 4. Various methods of determining effective pore diameter are described below.

Described another way, the effective pore diameter of the porous separating medium cross-sectioned perpendicular to the direction of flow of the eluant through the porous separating medium divided by radius of gyration of a long chain branched polymer of interest in the sample to be characterized is preferably in the range of from about 0.5 to about 50. As a point of reference, linear polystyrene of ten thousand, one hundred thousand and one million molecular weight has a radius of gyration in tetrahydrofuran of about three, about thirteen and about fifty nanometers respectively, See Yau et al., Modern Size-Exclusion Liquid Chromatography, page 36, 1979, John Wiley & Sons.

Figure 3:
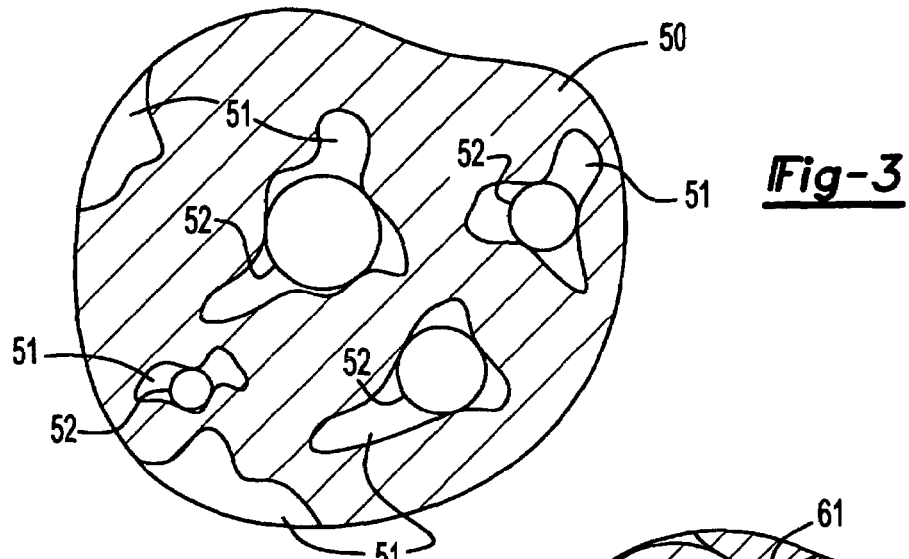
FIG. 3 is a cross-sectional microscopic depiction of a porous monolithic packing porous medium cross-sectioned perpendicular to the direction of flow of a liquid through the porous medium.

Referring now to FIG. 3, therein is shown a cross-sectional electron microscopic depiction of a porous monolithic packing porous separating medium 50 cross-sectioned perpendicular to the direction of flow of eluant through the porous medium. The pores 51 in the porous monolithic packing porous medium 50 are irregularly shaped and of different size. The effective pore diameter of the pores 51 is determined by the average size of a circle 52 that can be drawn in the pores 51 excluding any pores that are smaller than 30 Angstroms.

Figure 4:
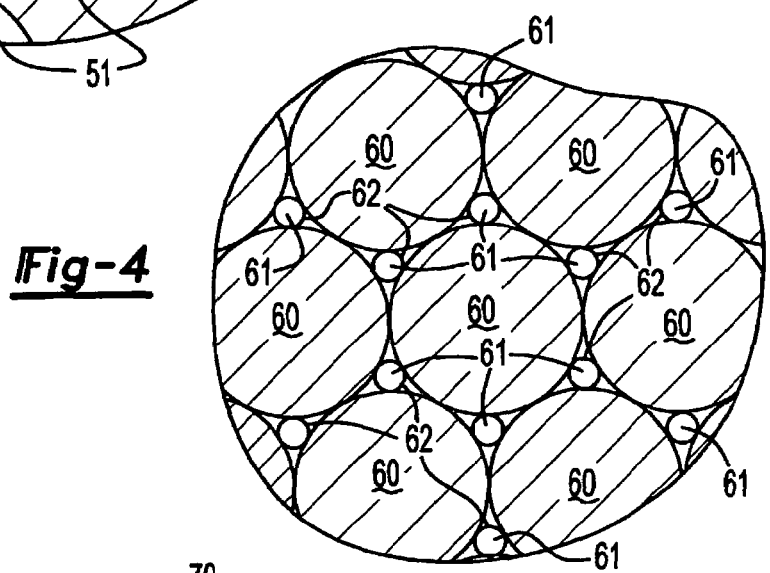
FIG. 4 is a cross-sectional microscopic depiction of a particle bed porous medium cross-sectioned perpendicular to the direction of flow of a liquid through the porous medium.

Referring now to FIG. 4, therein is shown a cross-sectional depiction of a porous separating medium comprising a bed of particles 60 cross-sectioned perpendicular to the direction of flow of eluant through the porous separating medium. The pores 61 in the bed of particles 60 are of uniform size because the particles 60 are of the same size. However, it should be understood that it is not critical in the instant invention that the particles 60 be essentially the same size. The effective pore diameter of the pores 61 is determined by the average size of a circle 62 that can be drawn in the pores 61 excluding any pores that are smaller than 30 Angstroms. When the particles 60 are of a uniform size, then the effective pore diameter of the pores 61 can simply be calculated as about 15% of the diameter of the particles 60.

Figure 5:
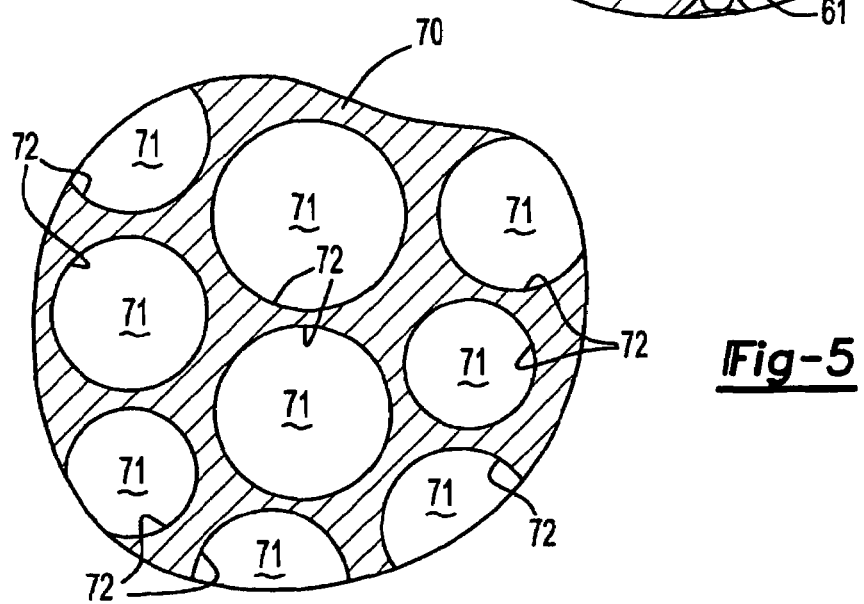
FIG. 5 is a cross-sectional microscopic depiction of an open cell foam structure porous medium cross-sectioned perpendicular to the direction of flow of a liquid through the porous medium.

Referring now to FIG. 5, therein is shown a cross-sectional electron microscopic depiction of an open cell foam structure 70 porous separating medium cross-sectioned perpendicular to the direction of flow of eluant through the porous separating medium. The effective pore diameter of the pores 71 in the structure 70 is determined by the average size of a circle 72 that can be drawn in the pores 71 excluding any pores that are smaller than 30 Angstroms. The pores 71 are shown as being circular in FIG. 4 for simplicity. However, in reality the pores 71 are often polygonal in shape.

Figure 6:
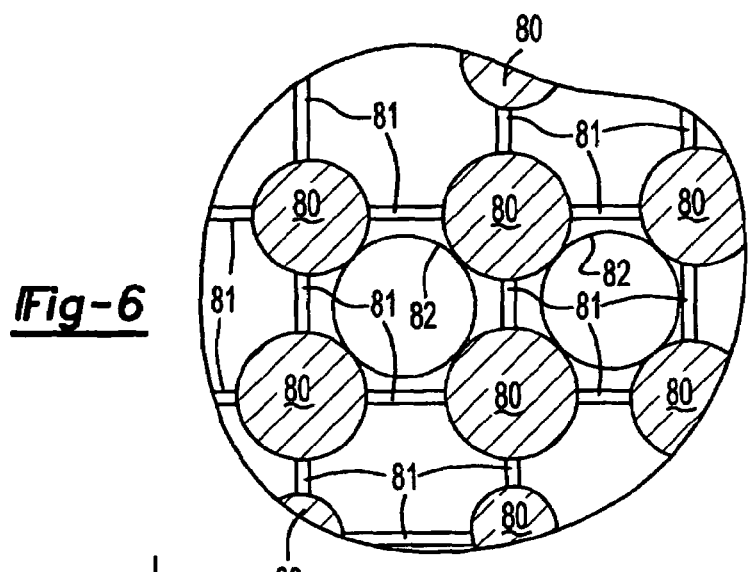
FIG. 6 is a cross-sectional microscopic depiction of a precipitated silica type of porous medium cross-sectioned perpendicular to the direction of flow of a liquid through the porous medium.

Referring now to FIG. 6, therein is shown a cross-sectional schematic depiction of a silica porous separating medium cross-sectioned perpendicular to the direction of flow of eluant through the porous separating medium. The silica porous separating medium comprises silica spheres 80 connected by silica strands 81. The effective pore diameter of the pores in the silica porous separating medium is determined by the average size of a circle 82 that can be drawn in the pores. The silica porous separating medium of the type shown in FIG. 6 can be made by the process described in U.S. Pat. No. 4,112,032 including hydrothermal treatment to increase mechanical strength and to improve pore size distribution as described by Iler, The Chemistry of Silica, Wiley, 1979, p 539-544.

Figure 10:
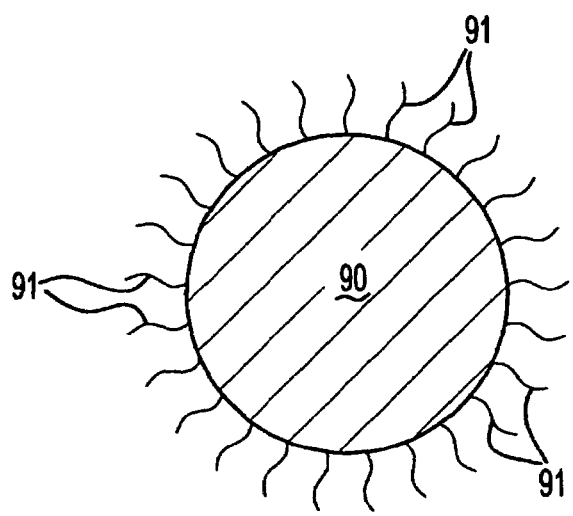
FIG. 10 is a cross-sectional depiction of a chromatographic packing particle having polymer chains extending from the surface of the particle.

Referring now to FIG. 10, therein is shown a cross-sectional depiction of a chromatographic packing particle 90 useful in the instant invention, the packing particle 90 having polymer chains 91 extending from the surface of the particle. Each of the polymer chains 91 most preferably consist of a minimum of 100 monomer units. Preferably, more than one half of the polymer chains 91 consist of a minimum of 300 monomer units. The polymer chains 91 can be attached to the particle 90 by the procedure outlined by von Verne and Patten, J. Am. Chem. Soc. 1999, 121, 7409-7410. The particle 90 can be any convenient particle such as silica or a synthetic polymer. It should also be understood that the exposed surfaces of a monolithic packing can also be treated so that such polymer chains extend from the surfaces of such a monolithic packing.

Referring still to FIG. 10, most preferably the kind of polymer of the polymer chains 91 is the same as the long chain branched polymer to be characterized. For example, if the long chain branched polymer to be characterized is polystyrene, then the polymer chains 91 are polystyrene. Preferably, the polymer of the polymer chains 91 is miscible with the solution of long chain branched polymer to be characterized.

Figure 7:
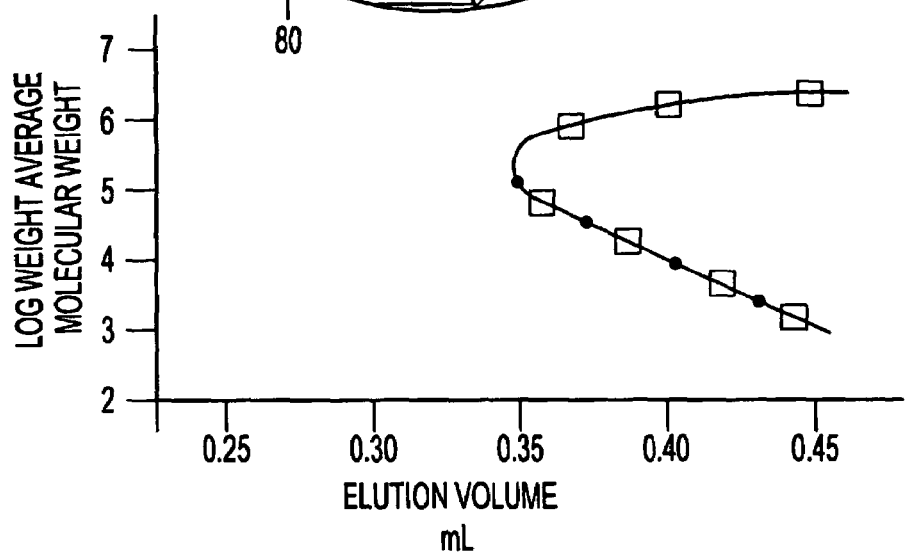
FIG. 7 is a plot of molecular weight v. elution volume for linear and long chain branched polystyrene standards analyzed at a flow rate of ten microliters per minute.

Referring again to FIG. 2, as the solution of the polymers is flowed through the porous separating medium contained in the column 15 by the flow of the liquid eluant 12 therethrough, the elution volume of the polymer will be a function of the molecular weight of the polymer, the flow rate of the liquid eluant 12 and the topology of the polymer. Referring now to FIG. 7, therein is shown a plot of log molecular weight (in terms of linear polystyrene equivalent weight average molecular weight in gram moles) v. elution volume for linear and long chain branched polystyrene samples analyzed at a flow rate of the liquid 12 (of FIG. 2) of ten microliters per minute (a linear velocity of 0.6 millimeters per minute) using a 4.6 millimeter internal diameter by fifty millimeter long column 15 (of FIG. 2) containing porous monolithic packing porous separating medium having an effective pore diameter of about 1,000 Angstroms. The square data points represent the peak elution volumes for the linear polystyrene samples. The dot data points represent the peak elution volumes of the long chain branched polystyrene samples.

It should be understood that the term "linear velocity" used herein means the linear velocity of the eluant in the chromatography column assuming that the column is not packed and assuming plug flow. Referring now to FIG. 2, of course, the actual linear velocity of the liquid 12 through the monolithic porous separating medium in column 15 is faster because the fraction of space in the column that comprises flow channels is less than the volume of the column 15. Never-the-less, the above stated definition of "linear velocity" is used herein for simplicity and to be consistent with the use of this term in the literature of Liquid Chromatography as the "superficial or empty-tube velocity", see J. Chromatography Library, Vol. 22A, page A38.

Figure 8:
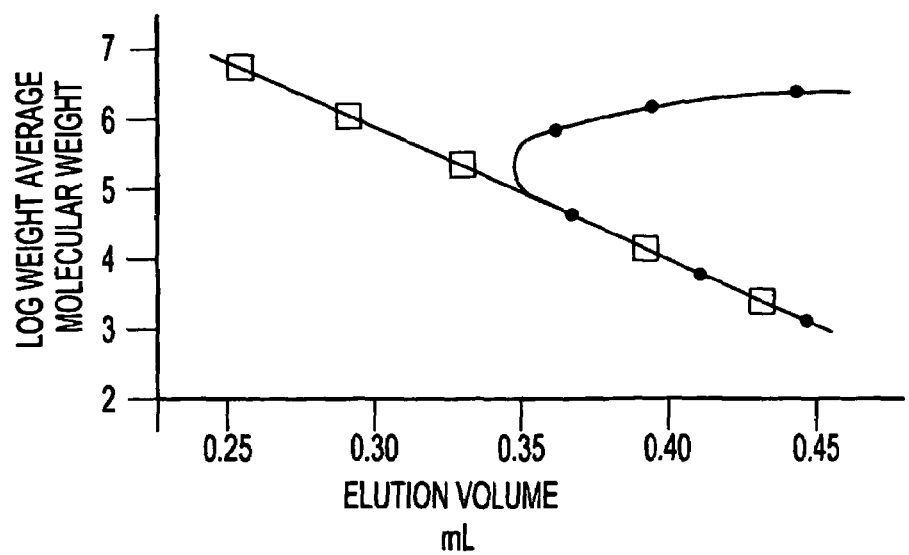
FIG. 8 is a plot of molecular weight v. elution volume for linear and long chain branched polystyrene standards analyzed at a flow rate of fifty microliters per minute.

Referring now to FIG. 8, therein is shown a plot of log molecular weight (in terms of linear polystyrene equivalent weight average molecular weight in gram moles) v. elution volume for the linear and long chain branched polystyrene samples analyzed at a flow rate of the liquid 12 (of FIG. 2) of fifty microliters per minute (a linear velocity of 3 millimeters per minute) using the same 4.6 millimeter internal diameter by fifty millimeter long column 15 containing porous monolithic packing porous separating medium as FIG. 7. The square data points represent peak elution volumes for the linear polystyrene samples. The dot data points represent peak elution volumes for the long chain branched polystyrene samples.

Figure 9:
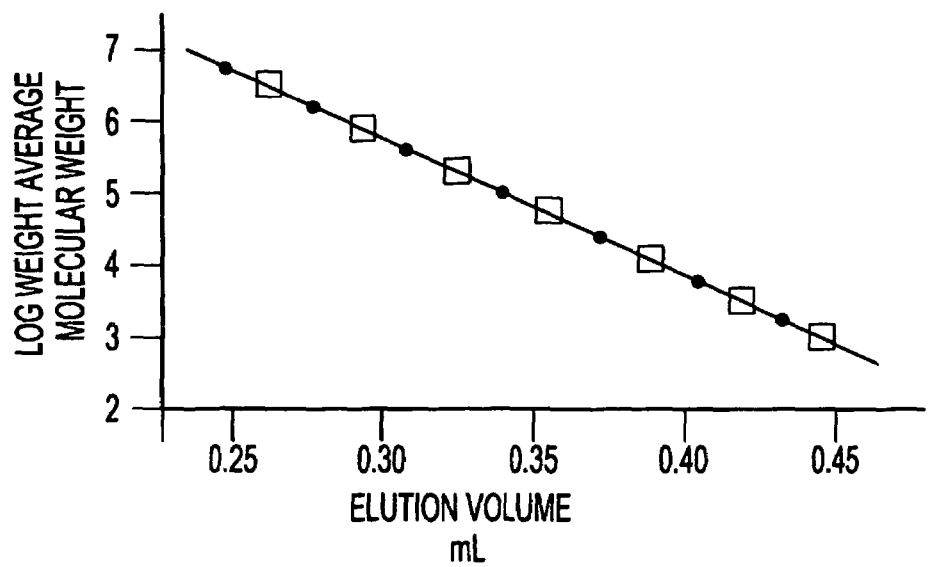
FIG. 9 is a plot of molecular weight v. elution volume for linear and long chain branched polystyrene standards analyzed at a flow rate of two hundred microliters per minute.

Referring now to FIG. 9, therein is shown a plot of log molecular weight (in terms of linear polystyrene equivalent weight average molecular weight in gram moles) v. elution volume for linear and long chain branched polystyrene standards analyzed at a flow rate of the liquid 12 (of FIG. 2) of two hundred microliters per minute (a linear velocity of 12 millimeters per minute) using the same 4.6 millimeter internal diameter by fifty millimeter long column as FIGS. 7 and 8. The square data points represent peak elution volumes for the linear polystyrene samples. The dot data points represent the peak elution volumes for the long chain branched polystyrene samples.

Referring still to FIG. 9, all of the data points lay on a straight line just as expected as if the mechanism of separation in the column 15 (of FIG. 2) were Hydrodynamic Chromatography. Referring now to FIG. 7, it will be noted that for log weight average molecular weight above about 5, there are no data points for long chain branched polymer. Long chain branched polymer having a log weight average molecular weight above about 5 may have become trapped in the column 15 (of FIG. 2) under these conditions (or at least such polymer has an elution volume greater than 0.45 milliliters).

When using the relatively fast flow rate of FIG. 9, there is no apparent separation of the linear and the long chain branched polymers on the column 15 (of FIG. 2). When using the intermediate flow rate of FIG. 8, there is a substantial and surprising separation between the linear and the long chain branched polymers. The optimum flow rate of the liquid eluant 12 (of FIG. 2) in the instant invention in order to obtain the optimum separation of polymers depends, of course, on the specific system used and can be relatively easily determined by experimentation.

It is believed that the instant invention can be used to separate not only linear (and short chain branched) polymer from long chain branched polymer but also two different long chain branched polymers even if they have the same molecular weight and are the same type provided they have different topology. For example, it is believed that the instant invention can be used to separate a "T" topology polystyrene of one million molecular weight from an "H" topology polystyrene of one million molecular weight.

Referring to FIG. 8, the porous separating medium used in the column 15 (of FIG. 2) to generate the data shown does not appear to be effective for log weight average molecular weights less than about 5. However, if the effective pore diameter of the porous medium used in the column 15 (of FIG. 2) is reduced, then the process of the instant invention can be used to characterize samples having long, chain branched polymer of interest of lower log weight average molecular weight.

Referring still to FIG. 8, polymer eluting at an elution volume of greater than about 0.34 milliliters may be an indication of a relatively high molecular weight long chain branched polymer or a relatively lower molecular weight polymer. This dichotomy is preferably solved by subjecting the successive volumes of the liquid eluant 12 (of FIG. 2) flowing from the detector 16 (of FIG. 2) to a separation technique capable of separating macromolecules based on molecular size, for example, size exclusion chromatography (SEC).

Referring now to FIG. 2, SEC eluant 22, for example, tetrahydrofuran, contained in SEC eluant reservoir 23 is pumped by second pump 24 through second injection valve 17, through SEC column 25, through second refractive index detector 26, through third detector 27 (such as a low-angle light scattering detector or a viscosity measuring detector) and then to third waste reservoir 28. First detector 16, second detector 26 and third detector 27 are connected to a general-purpose digital computer 29 by way of wires 30 (wireless communication is, of course, also suitable). The second injection valve 17 is periodically used to inject a successive elution volume of the liquid 12 onto the size exclusion chromatography column 25 to determine the hydrodynamic volume distribution of a polymer dissolved in the successive elution volume of the liquid 12. The relatively low flow rate of the liquid 12 through the column 15 permits a plurality of such SEC determinations during a single elution of a mixture of polymers from the column 15.

Referring still to FIG. 2, the computer 29 is programmed to periodically actuate the second injection valve 17 and to interpret and deconvolute the signals from the detectors 16, 26 and 27. For example, referring now to FIG. 7, polymer eluting at 0.40 milliliters can be determined to be 6.2 log weight average molecular weight long chain branched polymer and/or 4.0 log weight average molecular weight linear polymer because these two polymers have substantially different hydrodynamic volume as measured by SEC. When SEC is coupled with MTF, then it is preferable that the MTF system precede the SEC system as shown in FIG. 2. However, it should be understood that the SEC system can also precede the MTF system.

Scanning probe microscopy is a powerful technique for the characterization of the shape or topology of a single macromolecule, see Gerle et al., Macromolecules, 1999, 32, 2629-2637 and Prokhorova et al., Macromolecules, 1999, 32, 2653-2660. Referring to FIG. 2, the macromolecules of interest eluting from the size exclusion chromatography column 25 can be characterized by scanning probe microscopy in the instant invention by collecting a fraction of the eluant from the column 25 and then subjecting such fraction to scanning probe microscopy.

The process of the instant invention can be used to develop or produce a polymer, the polymer comprising long chain branched polymer. For example, different polymerization conditions (such as temperature, monomer feed rates, pressure, catalyst type and amount) can be studied to determine which conditions will produce a desired amount and type of long chain branching and the full scope of the instant invention includes the polymer so developed or produced. Similarly, the process of the instant invention can be used to develop a polymerization catalyst, the polymerization catalyst optimized to catalyze the polymerization of a polymer comprising long chain branched polymer. The full scope of the instant invention includes the catalyst so developed. For example, polymer produced by metalocene polymerization catalysts produced by combinatorial techniques can be analyzed using the process of the instant invention to identify the catalysts that produce the desired amount and type of long chain branching.

What is claimed is:

1. A process for characterizing a sample comprising a population of linear macromolecules of interest and a population of long chain branched macromolecules of interest, the process characterized by the steps of:
   (a) providing a sample comprising a population of linear macromolecules of interest comprising a select fraction (104) and a population of long chain branched macromolecules of interest comprising a select fraction (103), said select fractions being of similar size, the similar size of the fractions of interest being characterized so that these fractions will co-elute in a size exclusion chromatography experiment optimized so that the fractions are separated by hydrodynamic size and the separation is conducted under temperature and solvent conditions which produce equivalent results to that obtained when the separation is conducted under isothermal and isocratic conditions;
   (b) providing a flow through separating medium (100) and a liquid eluant (101) in which the macromolecules of interest dissolve, the separating medium defining a multiplicity of flow through channels (102), which are small enough in diameter so that when the eluant containing dissolved sample macromolecules of interest is caused to flow under pressure through the channels (102) over a certain linear velocity range, the select fraction (104) of the population of the linear macromolecules of interest will elute before the select fraction (103) of the population of the long chain branched macromolecules of interest whereby separate peak elution volumes (105) and (106) of said fractions of linear macromolecules and long chain branched macromolecules of interest are established for producing differentiation of the fraction of linear macromolecules from the fraction of long chain branched macromolecules;
   (c) determining said linear velocity range;
   (d) introducing the sample of dissolved linear macromolecules of interest and long chain branched macromolecules of interest into the liquid eluant;
   (e) flowing the liquid eluant under pressure through the channels of the separating medium at a linear velocity that is within the range specified in step (c), whereby the sample macromolecules of interest emerge from the separating medium separated into successive elution volumes of the liquid eluant, characterized by said linear macromolecules of interest eluting (105) before said similarly sized long chain branched macromolecules of interest (106); and
   (f) differentiating the linear macromolecules of interest from the long chain branched macromolecules of interest based on their successive elution volumes established in step (e).

2. The process of claim 1 wherein the linear macromolecules of interest are differentiated from the long chain branched macromolecules of interest by quantifying the concentration of same in each successive elution volume.

3. The process of claim 1 wherein said linear velocity range is determined on the lower end of the range by a velocity at which the sample macromolecules fail to elute from the separating medium, and at the upper end of the range by a velocity at which the long chain branched macromolecules elute in the same elution volume as the linear macromolecules of interest so that said linear macromolecules of interest cannot be differentiated from said long branched macromolecules of interest based on peak elution volume.

4. The process of claim 3 wherein the ratio of the peak elution volume of the long chain branched macromolecules of interest in the eluant to the peak elution volume of the dissolved linear macromolecules of interest in the eluant is greater than 1.

5. The process of claim 1 wherein a successive elution volume from step (e) is subjected to size exclusion chromatography to separate any macromolecules present based on hydrodynamic size.

6. The process of claim 5 wherein the macromolecules of interest eluting from the size exclusion chromatography separation medium are detected based on their concentration.

7. The process of claim 5 wherein the macromolecules of interest eluting from the size exclusion chromatography separation medium are detected by light scattering.

8. The process of claim 5 wherein the macromolecules of interest eluting from the size exclusion chromatography separation medium are detected by viscometry.

9. The process of claim 5 wherein the macromolecules of interest eluting from the size exclusion chromatography separation medium are detected based on multi-angle light scattering.

10. The process of claim 5 wherein the shape of the macromolecules of interest eluting from the size exclusion chromatography separating medium is characterized by scanning probe microscopy.

* * * * *